United States Patent [19]
Strukel

[11] Patent Number: 5,980,529
[45] Date of Patent: Nov. 9, 1999

[54] WORK TIP FOR SURGICAL ULTRASONIC DEVICE

[75] Inventor: Igor Strukel, New York, N.Y.

[73] Assignee: Vidda, Inc., New York, N.Y.

[21] Appl. No.: 08/932,610

[22] Filed: Sep. 17, 1997

[51] Int. Cl.⁶ ..................................................... A61F 9/00
[52] U.S. Cl. .......................... 606/107; 606/169; 604/19; 604/22
[58] Field of Search ................................ 606/169, 107; 604/19, 22

[56] References Cited

U.S. PATENT DOCUMENTS

| | | | |
|---|---|---|---|
| 5,057,119 | 10/1991 | Clark et al. | 606/169 |
| 5,242,385 | 9/1993 | Strunkel | 606/169 |
| 5,743,871 | 4/1998 | Strukel et al. | |

Primary Examiner—Michael Buiz
Assistant Examiner—(Jackie) Tan-Uyen T. Ho
Attorney, Agent, or Firm—Nims, Howes, Collison Hansen & Lackert

[57] ABSTRACT

A work tip for an ultrasonic surgical device has a distal end incorporating an upward projection that extends from about 10 to about 50% of the inner diameter of the hollow tip. An angled front face of the tip leads to an upper edge of the projection, which, under ultrasonic vibration assists in the break-up and emulsification of surgically displaced material, which is removed by vacuum through a passage in the work tip.

7 Claims, 5 Drawing Sheets

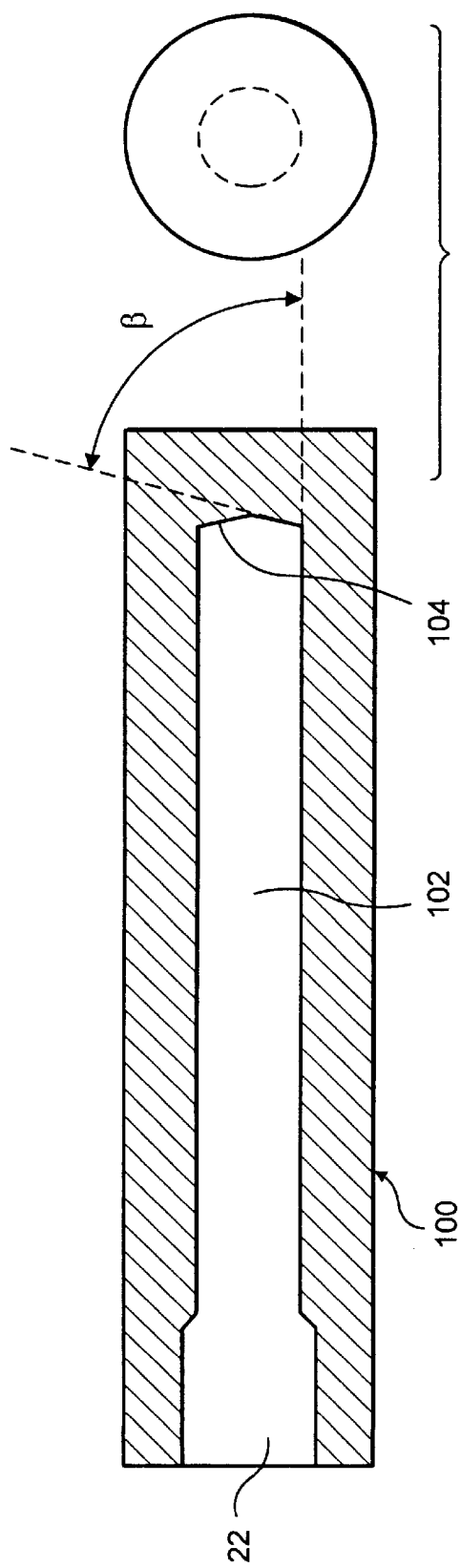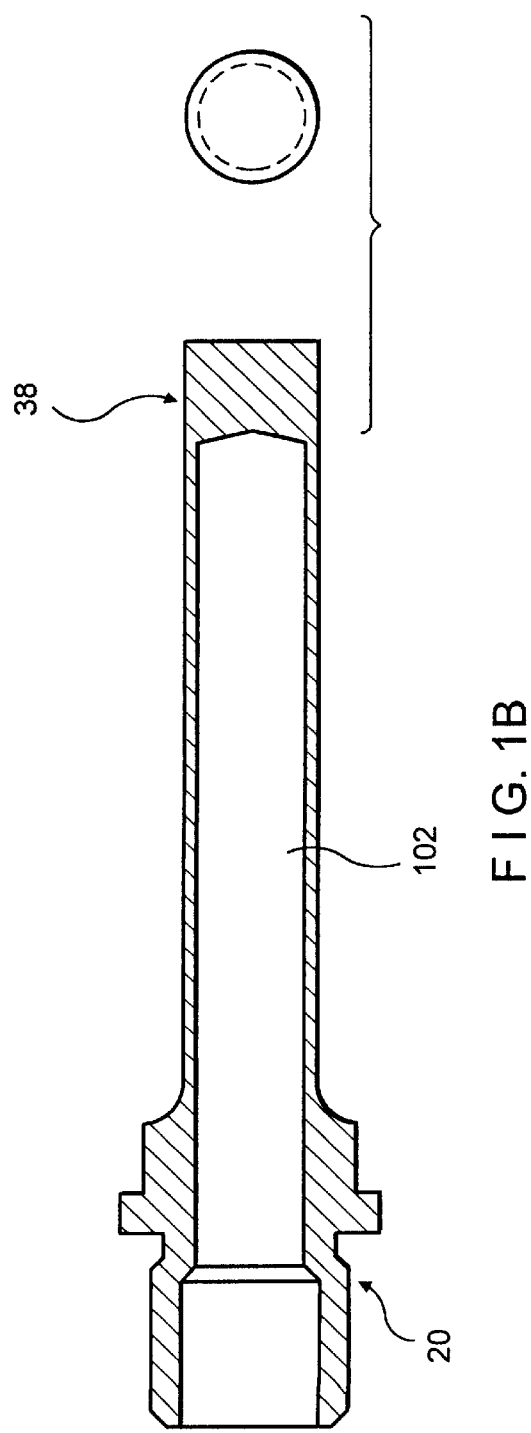

WORK TIP FOR SURGICAL ULTRASONIC DEVICE

TECHNICAL FIELD

This invention relates to improved work tips for ultrasonic surgical devices, and more particularly to work tips which are less susceptible to clogging during use.

BACKGROUND OF THE INVENTION

Various types of ultrasonic devices are used for surgical applications, for example, ophthalmological surgery for removing cataracts and other tissue. These devices employ a hollow work tip to transmit the ultrasonic energy which emulsifies the tissue to be removed. Such tips are typically made of titanium and usually have about 0.5 to about a 1 mm outside diameter and about a 0.6 to about 0.9 mm inner diameter.

In U.S. Pat. No. 5,242,385, an ultrasonic handpiece which is also capable of supplying an irrigation fluid to the operating site is described, with suction used for removing the material which has been emulsified by the ultrasonic transducer. A work tip is described which has an enlarged hollow front end forming a cavity into which the material to be emulsified is drawn and within which the material is emulsified. However, while the cavity promotes emulsification, the narrowing of the passage adjacent to the cavity creates a potential location for blockage of the tip to occur.

In U.S. Pat. No. 5,213,569, an ultrasonic phacoemulsification tip is described which has a rounded edge to prevent eye tissue damage, using an increased wall thickness, and to use a concave recess in the end face. The purpose is to more closely align the tip geometry for more effective utilization of the ultrasonic energy. However, this again results in a necking down in the tip which again can result in blockage.

BRIEF DESCRIPTION OF THE INVENTION

The present invention is directed to a surgical ultrasonic device work tip which is less susceptible to clogging during use, while using. In accordance with the invention, the work tip has an aspiration passage in the form of a hollow tube having an open end. A flow disruption projection extends into the aspiration passage at the open end to cause turbulence in the aspirated fluid and emulsified debris as they enter and pass by the open end. This turbulence encourages the breakup of the debris, thereby preventing clogging in the work tip. After the fluid and debris mix passes through the opening in the work tip, the material enters the aspiration passage where the flow disruption projection repeatedly impacts the material to create turbulence behind the flow disruption projection, preventing agglomeration of the debris in the passage.

OBJECT OF THE INVENTION

It is an object of the invention to provide a work tip for surgical ultrasonic devices which is less susceptible to clogging during use.

An additional object is to provide a process for the production of a work tip for surgical ultrasonic devices which is less susceptible to clogging during use.

Other objects and advantages of the present invention will become apparent upon reference to the following specification and annexed drawings.

BRIEF DESCRIPTION OF THE DRAWINGS

FIGS. 1A–C show a process for obtaining a work tip embodying the invention; FIG. 1A showing a breakaway side view and end view of a blank cylinder which has been drilled partially through; FIG. 1B showing the blank cylinder after it has been turned on a lathe to shape the work tip; and FIG. 1C showing the finished work tip after grinding to produce a beveled, open end.

DETAILED DESCRIPTION OF THE INVENTION

The present invention is a work tip for use with surgical ultrasonic devices. Various designs and processes for making them are depicted in FIGS. 1–4. These work tips are preferably made of titanium to resist wear and withstand operational stresses, although other materials are known and may be used.

Figure 1C:
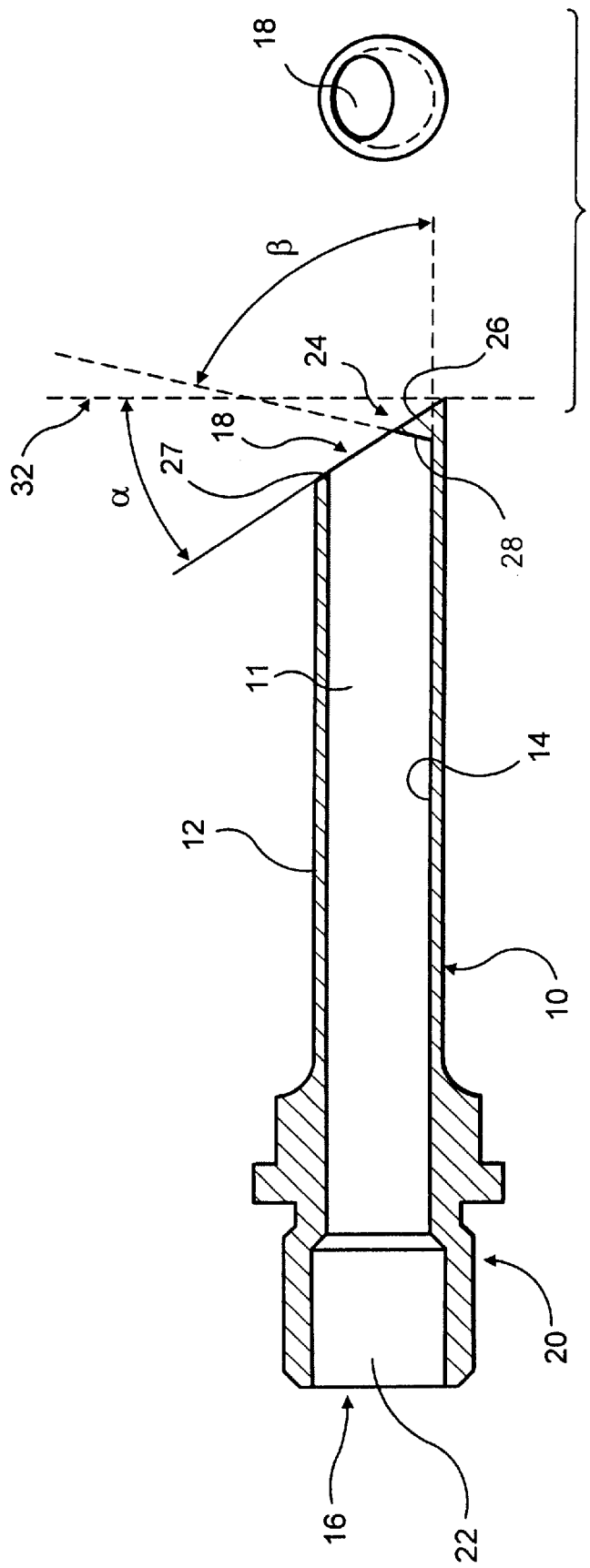
Figure 2A:
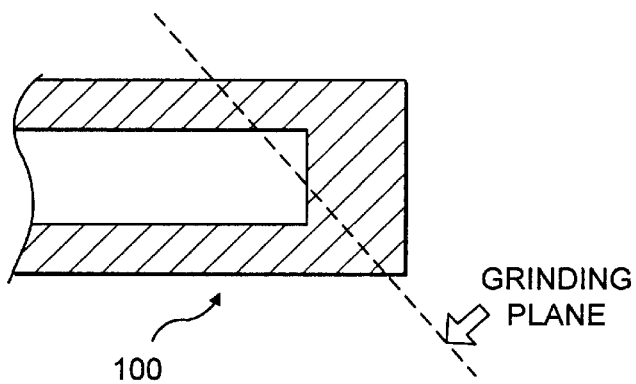
FIGS. 2A, 2B, 2C and 2D depict breakaway side views of the distal ends of alternative drilled blanks which may alternatively be used in place of the drilled blank of FIG. 1A for producing further embodiments of the invention.
Figure 2B:
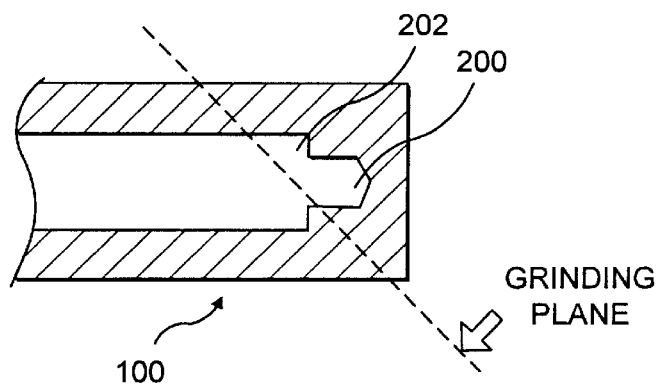
Figure 2C:
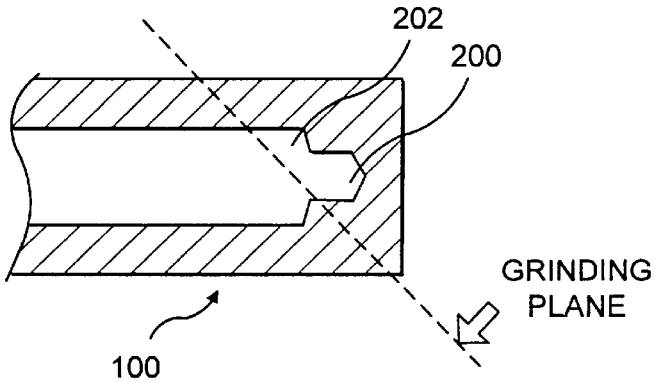
Figure 2D:
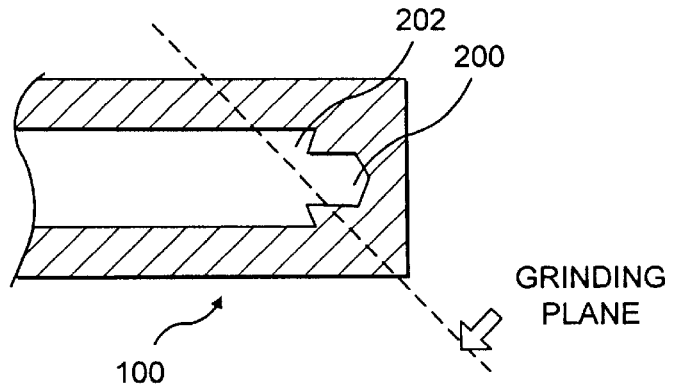

Referring to FIG. 1C, a work tip 10 is a hollow tube having an aspiration passage extending therethrough. The tube has an outer surface 12, an inner surface 14, a proximal end 16 and a distal end 18, each end having an opening leading to the passage. The distal end 18 of the tube contacts the tissue during use with ultrasonic energy supplied by a transducer (not shown), emulsifying the tissue which is then removed through the aspiration passage by suction.

Near the proximal end of the work tip, the outer surface has a recess 20 for attaching the tip to a hand-held ultrasonic device (not shown). Preferably, threads (not shown) are formed in the outer surface for attaching the tip to internal threads in the hand-held ultrasonic device, though other means for attaching the tip may be used.

The proximal end 16 is preferably concentric with the inner surface 14 and may have an enlarged entrance 22 for receiving a hollow connector from the hand-held ultrasonic device for connection of the hand-held ultrasonic device's suction to the hollow of the work tip.

The work tip has an upwardly extending projection 24 at the entrance to the aspiration passage. The projection 24 extends into the passage from about 10% to up to about 50% of the inner diameter of the opening. A forward surface 26 of the projection acts as part of a front face 27 of the tube end, with an interior surface 28 of the projection disposed at an angle B of from about 60° to about 135° relative to the inner surface 14 of the tube or to a longitudinal axis thereof.

Figure 4:
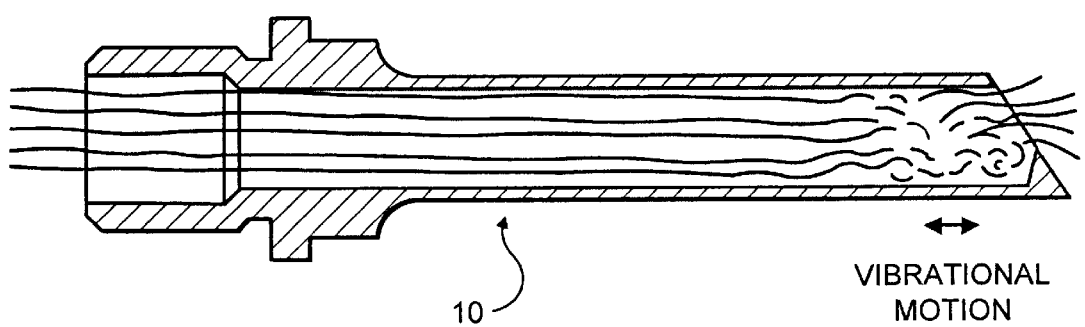
FIG. 4 is an illustration of the turbulence caused in the tip using the present invention.

The front face 27 at the distal end 18 is located at an angle α of about 15° to about 45° from the plane 32 perpendicular to the hollow tube. The distal end opening 18 is eccentric to the inner surface 14, because of the displacement caused by the outer surface of the projection. During use, as liquid and/or emulsified tissue is pulled through the work tip by suction, turbulence in the fluid flow is created behind the flow disruption projection 24 due to the action of the flow disruption projection 24 on the emulsified material, and the ultrasonic movement of the inner surface, which in essence pumps the material through the passage, as shown in FIG. 4. This prevents clogging of the work tip.

The work tips of the invention may be produced as shown in FIGS. 1–3, by a reasonably simple and relatively low cost process. In FIG. 1A, a blank tube 100 is provided. The blank tube 100 is a cylinder in which a concentric bore 102 has been drilled partially through the longitudinal length of the cylinder. Preferably, the bore 102 is the desired passage diameter of about 0.6 to about 0.9 mm. The bore 102 has an end wall 104 which may be flat surface (FIG. 2A) or a double bored flat surface (FIG. 2B), a concave conical surface (FIG. 2C) or a convex conical surface (FIG. 2D). Preferably, the angle B between the conical surface of the bore end and the inner surface is the angle chosen for the interior surface of the projection. The proximal opening of concentric bore 102 may be further drilled to provide a concentric enlarged portion 22. Preferably the large bore 22 is the desired diameter to receive a hollow connector from a hand-held ultrasonic device for connection of the hand-held ultrasonic device's suction to the hollow of the work tip.

The blank 100 is preferably turned on a lathe to produce the intermediate product depicted in FIG. 1B. The lathe operation reduces the overall thickness of the cylinder and provides near the opening of the bore means 20 for attaching the finished work tip to a hand-held ultrasonic device.

The intermediate product depicted in FIG. 1B is then ground or cut at an angle of about 15° to about 45° from the plane 32 on the end opposite the bore opening to produce the work tip 10 depicted in FIG. 1C. The plane of the cut or final grind passes through the side wall of the bore 102 and into a portion of the end wall 104 above the bottom of the bore, preferably removing the upper portion 38 of FIG. 1B to eliminate any upper projection 24 and to produce a flow disruption projection of from about 0.05 to about 0.30 mm into the hollow, though this can range from 0.05–0.5 mm, in a 1 mm diameter work tip.

FIG. 2 depicts partial views of some preferred embodiments of the blank 100 for use in the process of FIG. 1, along with the plane, shown by a dotted line, on which they are cut or ground after turning on the lathe. FIG. 2A depicts a blank having a flat-bottomed bore, the cut line producing a projection with an interior surface at 90° to the inner surface of the aspiration passage. FIGS. 2B–D depict blanks made by drilling first a smaller concentric bore 200, preferably of about 0.3 to 0.8 mm in diameter, followed by a larger concentric bore 202, preferably of about 0.6 to 0.9 mm in diameter, of lessor depth. FIG. 2B shows a larger concentric bore 202 having a flat bottom and a cut line producing a projection with an interior surface at 90° to the inner surface of the aspiration passage. FIG. 2C shows a larger concentric bore 202 having a conical concave bottom and a cut line producing a projection with an interior surface at about 110° to about 135° relative to the inner surface of the aspiration passage. FIG. 2D shows a larger concentric bore 202 having a conical concave bottom and a cut line producing a projection with an interior surface at 75° to the inner surface of the aspiration passage.

Figure 3A:
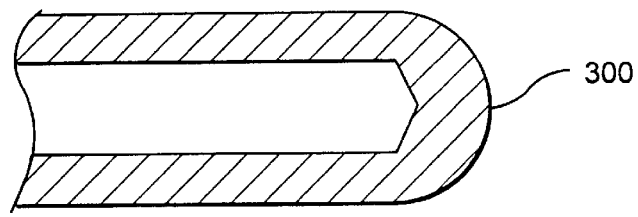
FIG. 3A shows the distal end of a work tip having an optional step of rounding the proximal end is employed between the steps of FIG. 1B and FIG. 1C.
Figure 3B:
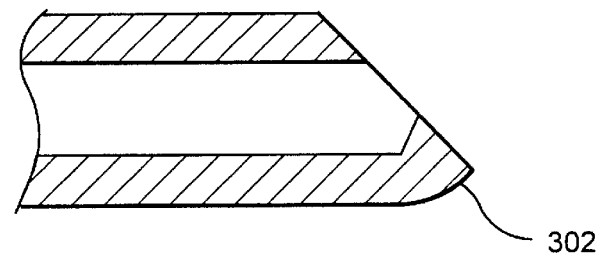
FIG. 3B shows the proximal end after grinding when the optional rounding step is employed.

FIG. 3 depicts an optional step in the process of producing the work tips. To avoid the potential for eye injury it is preferred to have a rounded end such that the ultrasonic energy, not the physical end of the tip, removes the desired tissue. This is achieved by radiusing the sharp edge of the tip. Preferably, the intermediate product shown in FIG. 1B is rounded on the end opposite the bore opening, producing the rounded end 300 depicted in FIG. 3A. The resultant work tip has a distal opening with a rounded exterior edge 302, as depicted in FIG. 3B. The embodiment depicted in FIG. 3B could also be produced by rounding after the cutting or grinding step.

Figure 5A:
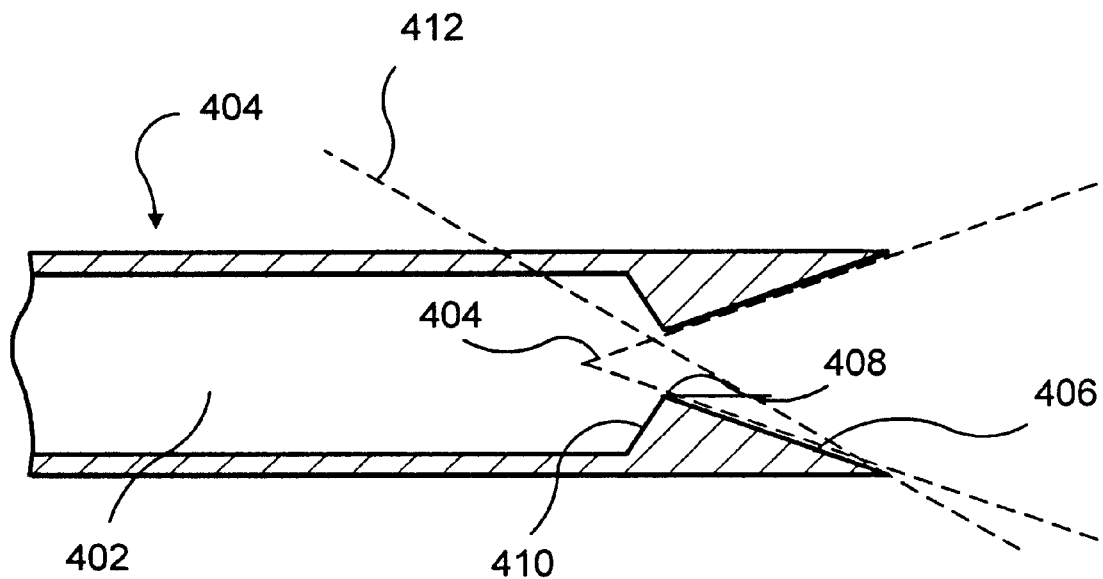
FIG. 5A is an illustration of an alternative embodiment of the invention, FIG. 5B being a front view of the work tip.
Figure 5B:
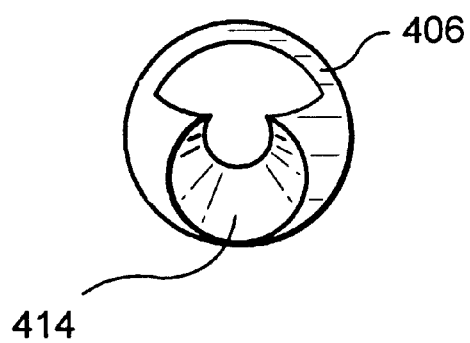

Referring to FIGS. 5A and 5B, an alternative embodiment of the invention is shown. In this embodiment, a blank 400 is an elongated cylinder of a size sufficient to allow for boring through both ends. The first drilling is made as described previously relative to FIGS. 2A–D, to produce a passage 402. However, instead of grinding the distal end to provide a flat outer surface, a second pointed drill, shown in phantom, as 404, is used to produce a beveled outer surface 406, and to achieve a sharp upper edge 408 on the upward projection 410. After grinding along the plane 412, the front surface 406 is shaped by the conical drill bit to have an indent 414 which acts like a scoop as shown in FIG. 5B to promote smooth passage of the removed material into the aspiration passage.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents that can be included within the spirit and scope of the following claims.

I claim:

1. A work tip for a surgical ultrasonic device comprising:
   a hollow tube having an inner surface defining an aspiration passage, a proximal end for connection to the ultrasonic device for vibrating the hollow tube and to a suction source for drawing material through the aspiration passage, a distal cutting end, a flow disruption projection disposed at an opening in the distal end, the projection extending upwardly into the aspiration passage for from about 10% to about 50% of an inner diameter of the opening, the projection having a front surface coincident with a front face of the tube, the front face of the tube extending diagonally across the tube, the projection having an interior surface within the tube, the front surface and interior surface intersecting to provide a sharp upper edge at an entrance to the aspiration passage, the interior surface disposed at an angle of from about 60° to 135° relative to a longitudinal axis of the tube.

2. The work tip according to claim 1, wherein the distal end is beveled at an angle of from about 15° to about 45° to the plane perpendicular to the hollow tube.

3. The work tip according to claim 1, wherein an exterior edge of the distal end is rounded.

4. The work tip according to claim 1, wherein the flow disruption projection has an interior surface disposed at an angle of from about 60° to about 90°.

5. The work tip according to claim 1, wherein the work tip is constructed of titanium.

6. The work tip according to claim 1 where the front surface is flat.

7. The work tip according to claim 1 where the front surface is indented to form a scoop.

* * * * *